United States Patent [19]

Cherpeck

[11] Patent Number: 5,637,119
[45] Date of Patent: Jun. 10, 1997

[54] SUBSTITUTED AROMATIC POLYALKYL ETHERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 581,658

[22] Filed: Dec. 29, 1995

[51] Int. Cl.$^6$ .......................... C10L 1/22; C07C 211/26; C07C 211/43
[52] U.S. Cl. .................. 44/384; 44/413; 44/424; 44/426; 44/427; 44/428; 564/336; 564/384; 564/389; 564/430; 564/441
[58] Field of Search ............................. 44/384, 413, 424, 44/427, 428; 564/384, 389, 430

[56] References Cited

U.S. PATENT DOCUMENTS

| | | | |
|---|---|---|---|
| 2,300,246 | 10/1942 | Chenick et al. | 44/428 |
| 3,182,085 | 5/1965 | Pitchforth | 564/389 |
| 3,293,297 | 12/1966 | Louvar et al. | 44/428 |
| 3,353,939 | 11/1967 | Cannon et al. | 44/384 |
| 3,434,814 | 3/1969 | Dubeck et al. | 44/413 |
| 3,544,637 | 12/1970 | Kober et al. | 564/430 |
| 3,702,862 | 11/1972 | Mine et al. | 564/430 |
| 3,849,085 | 11/1974 | Kreuz et al. | 44/78 |
| 3,877,889 | 4/1975 | Dix | 44/424 |
| 3,946,119 | 3/1976 | Kathawala | 564/389 |
| 4,014,937 | 3/1977 | Richardson | 564/389 |
| 4,191,537 | 3/1980 | Lewis et al. | 44/71 |
| 4,392,866 | 7/1983 | Sung et al. | 44/428 |
| 4,392,867 | 7/1983 | Sung et al. | 44/427 |
| 4,425,138 | 1/1984 | Davis | 44/413 |
| 4,881,945 | 11/1989 | Buckley | 44/72 |
| 5,112,364 | 5/1992 | Rath et al. | 44/418 |
| 5,409,507 | 4/1995 | Cherpeck | 44/413 |

Primary Examiner—Ellen M. McAvoy
Attorney, Agent, or Firm—Claude J. Caroli

[57] ABSTRACT

Substituted aromatic polyalkyl ethers having the formula:

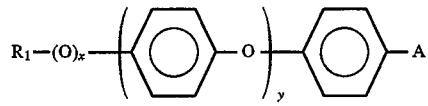

wherein $R_1$ is a polyalkyl group having an average molecular weight of about 450 to about 5,000;

A is nitro, amino, cyano, aminomethyl, N-alkylamino or N-alkylaminomethyl wherein the alkyl group contains from about 1 to about 6 carbon atoms, or N,N-dialkylamino or N,N-dialkylaminomethyl wherein each alkyl group independently contains from about 1 to about 6 carbon atoms x is an integer from about 0 to about 1; and y is an integer from about 0 to about 10 with the proviso that one of x and y must be 0 and the other must be greater than 0.

The substituted aromatic polyalkyl ethers of the present invention are useful as fuel additives for the prevention and control of engine deposits.

30 Claims, No Drawings

SUBSTITUTED AROMATIC POLYALKYL ETHERS AND FUEL COMPOSITIONS CONTAINING THE SAME

BACKGROUND OF THE INVENTION

1. Field of the Invention

This invention provides novel fuel-soluble substituted aromatic polyalkyl ether fuel additives which are useful for the prevention and control of engine deposits, particularly intake valve deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to about 0.25 volume percent of a high molecular weight aliphatic hydrocarbon-substituted phenol in which the aliphatic hydrocarbon radical has an average molecular weight in the range of about 500 to about 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Polyether amine fuel additives are also well known in the art for the prevention and control of engine deposits. These polyether additives have a polyoxyalkylene "backbone", i.e., the polyether portion of the molecule consists of repeating oxyalkylene units. U.S. Pat. No. 4,191,537, issued Mar. 4, 1980 to Lewis et al., for example, discloses a fuel composition comprising a major portion of hydrocarbons boiling in the gasoline range and from 30 to 2,000 ppm of a hydrocarbyl polyoxyalkylene aminocarbamate having a molecular weight from about 600 to 10,000, and at least one basic nitrogen atom. The hydrocarbyl polyoxyalkylene moiety is composed of oxyalkylene units having from 2 to 5 carbon atoms in each oxyalkylene unit. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Similarly, U.S. Pat. No. 4,881,945, issued Nov. 21, 1989 to Buckley, discloses a fuel composition comprising a hydrocarbon boiling in the gasoline or diesel range and from about 30 to about 5,000 parts per million of a fuel soluble alkylphenyl polyoxyalkylene aminocarbamate having at least one basic nitrogen and an average molecular weight of about 800 to 6,000 and wherein the alkyl group contains at least 40 carbon atoms.

In U.S. Pat. No. 5,112,364, issued May 12, 1992 to Rath et al., discloses gasoline-engine fuels which contain small amounts of a polyetheramine and/or a polyetheramine derivative, wherein the polyetheramine is prepared by reductive amination of a phenol-initiated or alkylphenol-initiated polyether with ammonia or a primary amine.

It has now been discovered that certain substituted aromatic polyalkyl ethers provide excellent control of engine deposits, especially intake valve deposits, when employed as fuel additives in fuel compositions.

SUMMARY OF THE INVENTION

The present invention provides novel fuel-soluble substituted aromatic polyalkyl ether fuel additives which are useful for the prevention and control of engine deposits, particularly intake valve deposits.

The fuel-soluble substituted aromatic polyalkyl ethers of the present invention have the formula:

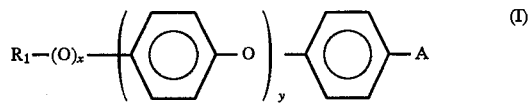

wherein $R_1$ is a polyalkyl group having an average molecular weight of about 450 to about 5,000; A is nitro, amino, cyano, aminomethyl, N-alkylamino or N-alkylaminomethyl wherein the alkyl group contains from about 1 to about 6 carbon atoms, or N,N-dialkylamino or N,N-dialkylaminomethyl wherein each alkyl group independently contains from about 1 to about 6 carbon atoms; x is an integer from about 0 to about 1; and y is an integer from about 0 to about 10 with the proviso that one of x and y must be 0 and the other must be greater than 0.

The present invention further provides a fuel composition comprising a major amount of hydrocarbons boiling in the gasoline or diesel range and an effective deposit-controlling amount of a substituted aromatic polyalkyl ether of the present invention.

The present invention additionally provides a fuel concentrate comprising an inert stable oleophilic organic solvent boiling in the range of from about 150° F. to about 400° F. (about 65° C. to about 205° C.) and from about 10 to about 70 weight percent of a substituted aromatic polyalkyl ether of the present invention.

Among other factors, the present invention is based on the surprising discovery that certain substituted aromatic polyalkyl ethers provide excellent control of engine deposits, especially on intake valves, when employed as fuel additives in fuel compositions.

DETAILED DESCRIPTION OF THE INVENTION

The substituted aromatic polyalkyl ethers of the present invention have the general formula:

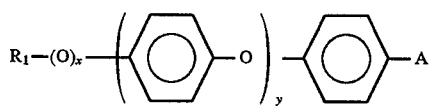

wherein $R_1$, A, x and y are as defined above.

In Formula I, above, $R_1$ is preferably a polyalkyl group having an average molecular weight in the range of about 700 to about 5,000, more preferably about 700 to about 3,000, and most preferably about 900 to about 2,500.

When A is an N-alkylamino group, the alkyl group of the N-alkylamino moiety preferably contains 1 to 4 carbon atoms. More preferably, the N-alkylamino is N-methylamino or N-ethylamino.

Similarly, when A is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

Preferably, A is nitro, amino, cyano, or aminomethyl. More preferably, A is nitro, amino or aminomethyl. Most preferably, A is nitro or amino.

As noted above, x is an integer from about 0 to about 1 and y is an integer from about 0 to about 10, with the proviso that one of x and y must be 0 and the other must be greater than 0. Thus, when x is 0, then y is about 1 to about 10 and when x is about 1, then y is 0.

The compounds of the present invention will generally have a sufficient molecular weight so as to be non-volatile at normal engine intake valve operating temperatures (about 200°–250° C.). Typically, the molecular weight of the compounds of this invention will range from about 900 to about 5,500, preferably from 900 to 3,500.

Definitions

As used herein the following terms have the following meanings unless expressly stated to the contrary.

The term "amino" refers to the group: —$NH_2$.

The term "cyano" refers to the group: —CN.

The term "nitro" refers to the group: —$NO_2$.

The term "N-alkylamino" refers to the group: —$NHR_a$ wherein $R_a$ is an alkyl group. The term "N,N-dialkylamino" refers to the group: —$NR_bR_c$ wherein $R_b$ and $R_c$ are alkyl groups.

The term "aminomethyl refers to the group —$CH_2NH_2$. The term "N-alkylaminomethyl" refers to the group: —$CH_2NHR_d$ wherein $R_d$ is an alkyl group. The term "N,N-dialkylaminomethyl" refers to the group: —$CH_2NR_eR_f$ wherein $R_e$ and $R_f$ are alkyl groups.

The term "alkyl" refers to both straight- and branched-chain alkyl groups.

The term "polyalkyl" refers to alkyl groups which are generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

General Synthetic Procedures

The substituted aromatic polyalkyl ethers of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated.

Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxyl group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the polyalkyl aromatic esters of this invention having an amino group on the aromatic moiety will generally be prepared from the corresponding nitro derivative. Accordingly, in many of the following procedures, a nitro group will serve as a protecting group for the amino moiety.

Moreover, the compounds of this invention having a —$CH_2NH_2$ group on the aromatic moiety will generally be prepared from the corresponding cyano derivative, —CN. Thus, in many of the following procedures, a cyano group will serve as a protecting group for the —$CH_2NH_2$ moiety.

The substituted aromatic polyalkyl ethers of the present invention having the formula:

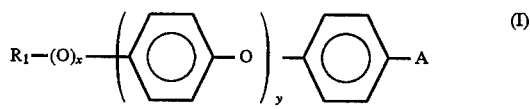

wherein x is about 1 and y is 0, may be prepared by conventional reaction conditions by first reacting a polyalkyl monohydroxy alcohol having the formula:

wherein $R_1$ is a polyalkyl group as defined above, with a suitable base, such as KOH, NaH, or KH, followed by reaction with an aromatic compound having the formula:

wherein B is nitro or cyano, and C is a halide, preferably a fluoride or chloride, and more preferably fluoride. Such aromatic compounds of Formula III are well known to one skilled in the art to be readily available commercially. For example, these compounds can be purchased from Aldrich Chemical Company, Inc. Where desired, the resulting nitro or cyano aromatic ethers of Formula I may be reduced to the corresponding amino or aminomethyl compound.

The substituted aromatic polyalkyl ethers of Formula I wherein x is 0 and y is 1 may be prepared by first reacting a polyalkyl phenol of the formula:

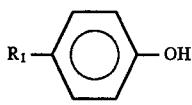
(IV)

wherein $R_1$ is a polyalkyl group as defined above, with a base, such as NaOH, NaH, or KH, followed by reaction with a nitro or cyano aramatic halide of Formula III. The resulting nitro or cyano aromatic ethers may then be reduced to the corresponding amino or aminomethyl compounds using conventional hydrogenation conditions.

The substituted aromatic polyalkyl ethers of Formula I wherein x is 0 and y is 2 to 10, may be prepared by first reacting a polyalkyl phenol of Formula IV with a base, such as NaOH, NaH, or KH, followed by reaction with a suitably protected hydroxyaromatic halide of the formula:

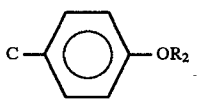
(V)

wherein C is a halide, such as fluoride, and $R_2$ is a suitable hydroxy protecting group, such as benzyl, to give an aromatic ether of the formula:

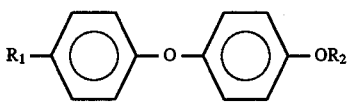
(VI)

Removal of the benzyl or other hydroxy protecting group, $R_2$, by conventional methods provides the free hydroxy compound of the formula:

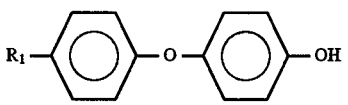
(VII)

Reaction of the hydroxy compound of Formula VII with a nitro or cyano aromatic halide of Formula III provides an aromatic ether compound to Formula I wherein y is 2. Repeating the above procedure by reacting a compound of Formula VII with a protected by hydroxyaromatic halide of Formula V provides compounds wherein y is greater than 2.

The polyalkyl substituent on the monohydroxy alcohols or polyalkylphenols may be generally derived from an appropriate olefin or olefin mixture. A particularly preferred class of olefins for use in preparing monohydroxy alcohols and phenols useful in this invention are polyolefin polymers. Polyolefin polymers are polymers comprising a major amount of $C_2$ to $C_5$ mono-olefins, e.g., ethylene, propylene, butylene, isobutylene, and pentylene.

The polymers can be homopolymers such as polyisobutylene as well as copolymers of two or more such olefins such as copolymers of: ethylene and propylene, butylene, and isobutylene, etc. Other copolymers include those in which a minor amount of the copolymer monomers, e.g., from about 1 to about 20 mole percent is a $C_4$ to $C_8$ nonconjugated diolefin, e.g., a copolymer of isobutylene and butadiene or a copolymer of ethylene, propylene, and 1,4-hexadiene, etc.

A particularly preferred class of olefin polymers comprises the polybutenes, which are prepared by polymerization of one or more of 1-butene, 2-butene, and isobutene. Especially desirable are polybutenes containing a substantial proportion of units derived from isobutene. The polybutene may contain minor amounts of butadiene which may or may not be incorporated in the polymer. Most often the isobutene units constitute about 80%, preferably at least about 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as U.S. Pat. No. 3,912,764. The above are incorporated by reference for their disclosures of suitable polybutenes.

One type of suitable polyolefins are those containing an alkylvinylidene isomer present in an amount at least about 20%, and preferably at least about 50%, of the total polyolefin composition. The preferred alkylvinylidene isomers include methylvinylidene and ethylvinylidene, more preferably the methylvinylidene isomer.

Accordingly, high molecular weight polyolefins which may be used in this invention include polyisobutenes which comprise at least about 20% of the more reactive methylvinylidene isomer, preferably at least about 50%, and more preferably at least about 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808, the disclosures of which are incorporated herein by reference.

Examples of suitable polyisobutenes having a high methylvinylidene content include Ultravis 10, a polyisobutene having a molecular weight of about 950 and a methylvinylidene content of about 76%, and Ultravis 30, a polyisobutene having a molecular weight of about 1,300 and a methylvinylidene content of about 74%, both available from British Petroleum.

Preferred monohydroxy alcohols suitable for the present invention include polyisobutyl alcohol and polypropyl alcohol.

Many of the polyalkyl alcohols are commercially available and the others can be readily prepared from the corresponding olefins by conventional procedures. Suitable procedures for preparing alcohols from olefins are described, for example, in I. T. Harrison and S. Harrison, *Compendium of Organic Synthetic Methods*, pp. 119–122, Wiley-Interscience, New York (1971) and references cited therein. Further disclosures thereof will be found, for example, in U.S. Pat. Nos. 4,859,210; 4,881,945; 5,5055,607; and 5,300,701, the disclosures of which are incorporated herein by reference.

As noted above, the monohydroxy alcohol is reacted with an aromatic compound of Formula III to form the substituted aromatic polyalkyl ethers of the present invention. Such aromatic compounds are preferably 4-cyanofluorobenzene, and 4-nitrofluorobenzene.

In a preferred embodiment of the present invention, y is an integer of from about 1 to about 10, i.e., containing from about 1 to about 10 recurring aromatic phenoxy groups. Reaction conditions for preparing such compounds will be readily apparent to one skilled in the art and references describing these kinds of reactions may be found, for example, in A. A. Moroz and M. S. Shvartsberg, "The Ullman Ether Condensation" Russian Chemical Reviews, 43 (8), 1974, the disclosure of which is incorporated herein by reference.

As noted above, the resulting product of the above reactions may then reduced by conventional procedures known in the art to yield the amino or aminomethyl substituted aromatic polyalkyl ethers (Formula I) of the present invention. For example, reduction of the aromatic cyano or nitro compounds to the corresponding amines is well known in the art. See, for example, the article entitled, "*Amination by Reduction*" in Kirk-Othmer "*Encyclopedia of Chemical Technology*", Second Edition, Vol. 2, pp 76–99. Generally, such reductions can be carried out with, for example, hydrogen, carbon monoxide, or hydrazine, (or mixtures of the same) in the presence of metallic catalysts such as palladium, platinum, and its oxides, nickel, copper chromite, etc. Co-catalysts such as alkali or alkaline earth metal hydroxides or amines (including amino phenols) can used in these catalyzed reductions.

Reductions can also be accomplished through the use of reducing metals in the presence of acids, such as hydrochloric acid. Typical reducing metals are zinc, iron, and tin; salts of these metals can also be used.

Typically, the amino or aminomethyl substituted aromatic polyalkyl aromatic ethers of the present invention are obtained by reduction of the corresponding nitro or cyano compound with hydrogen in the presence of a metallic catalyst such as palladium. This reduction is generally carried out at temperatures of about 20° C. to about 100° C., typically, about 20° C. to about 40° C., and hydrogen pressures of about atmospheric to about 200 psig, typically, about 20 to about 80 psig. The reaction time for reduction usually varies between about 5 minutes to about 24 hours. Substantially, inert liquid diluents and solvents, such as ethanol, cyclohexane, ethyl acetate, toluene, etc, can be used to facilitate the reaction. The substituted aromatic polyalkyl ethers can then be obtained by well-known techniques such as distillation, filtration, extraction, and so forth.

Fuel Compositions

The substituted aromatic polyalkyl ethers of the present invention are useful as additives in hydrocarbon fuels to prevent and control engine deposits, particularly intake valve deposits. Typically, the desired deposit control will be achieved by operating an internal combustion engine with a fuel composition containing a substituted aromatic polyalkyl ether of the present invention. The proper concentration of additive necessary to achieve the desired deposit control varies depending upon the type of fuel employed, the type of engine, and the presence of other fuel additives.

In general, the concentration of the substituted aromatic polyalkyl ethers of this invention in hydrocarbon fuel will range from about 50 to about 2,500 parts per million (ppm) by weight, preferably from about 75 to about 1,000 ppm. When other deposit control additives are present, a lesser amount of the present additive may be used. Furthermore, lower concentrations of, for example, from about 30 to about 70 ppm may be preferred when the present additives are employed as carburetor detergents only.

The substituted aromatic polyalkyl ethers of the present invention may be formulated as a concentrate using an inert stable oleophilic (i.e., dissolved in gasoline) organic solvent boiling in the range of from about 150° F. to about 400° F. (from about 65° C. to about 205° C.). Preferably, an aliphatic or an aromatic hydrocarbon solvent is used, such as benzene, toluene, xylene, or higher-boiling aromatics or aromatic thinners. Aliphatic alcohols containing from about 3 to about 8 carbon atoms, such as isopropanol, isobutylcarbinol, n-butanol, and the like, in combination with hydrocarbon solvents are also suitable for use with the present additives.

In the concentrate, the amount of the additive will generally range from about 10 to about 70 weight percent, preferably from about 10 to about 50 weight percent, more preferably from about 10 to about 25 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators, and demulsifiers may be present.

In diesel fuels, other well-known additives can be employed, such as pour point depressants, flow improvers, cetane improvers, and the like. A fuel-soluble, nonvolatile carrier fluid or oil may also be used with the substituted aromatic polyalkyl ethers of this invention. The carrier fluid is a chemically inert hydrocarbon-soluble liquid vehicle which substantially increases the nonvolatile residue (NVR) or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis and polyesters, such as those described, for example, in U.S. Pat. Nos. 3,756,793 and 5,004,478, and in European Patent Application Nos. 356,726 and 382,159.

These carrier fluids are believed to act as a carrier for the fuel additives of the present invention and to assist in removing and retarding deposits. The carrier fluid may also exhibit synergistic deposit control properties when used in combination with the substituted aromatic polyalkyl ethers of this invention.

The carrier fluids are typically employed in amounts ranging from about 100 to about 5,000 ppm by weight of the hydrocarbon fuel, preferably from about 400 to about 3,000 ppm of the fuel. Preferably, the ratio of carrier fluid to deposit control additive will range from about 0.5:1 to about 10:1, more preferably from about 1:1 to about 5:1, most preferably from about 2:1 to about 4:1.

When employed in a fuel concentrate, carrier fluids will generally be present in amounts ranging from about 20 to about 60 weight percent, preferably from about 30 to about 50 weight percent.

EXAMPLES

The following examples are presented to illustrate specific embodiments of the present invention and synthetic preparations thereof and should not be interpreted as limitations upon the scope of the invention.

EXAMPLE 1

Preparation of Polyisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 milliliters of boron trifluoride etherate was added dropwise. 1040 grams of Ultravis 10 polyisobutene (molecular weight 950, 76% methylvinylidene, available from British Petroleum) was dissolved in 1,863 milliliters of hexane. The polyisobutene was added to the reaction at a rate to maintain the temperature between 22°–27° C. The reaction mixture was stirred for 16 hours at room temperature. Then, 400 milliliters of concentrated ammonium hydroxide was added followed by 2,000 milliliters of hexane. The reaction mixture was washed with water (3×2,000 milliliters), dried over magnesium sulfate, filtered and the solvents removed under vacuum to yield 1,056.5 grams of a crude reaction product. The crude reaction product was determined to contain 80% of the desired product by proton NMR and chromatography on silica gel eluting with hexane, followed by hexane; ethylacetate; ethanol (93:5;2).

EXAMPLE 2

Preparation of

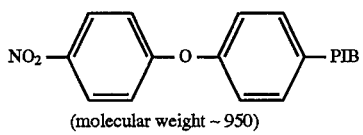

(molecular weight ~ 950)

To a flask equipped with a magnetic stirrer, reflux condensor, nitrogen inlet and addition funnel was added 24.4 grams of a 35 weight percent dispersion of potassium hydride in mineral oil. The mineral oil was removed from the potassium hydride with anhydrous hexane. 1 Liter of anhydrous tetrahydrofuran was added and the resulting suspension was cooled to 0° C. 4-polyisobutyl phenol (211.2 grams, prepared as in Example 1 ) dissolved in 1 liter of anhydrous tetrahydrofuran was added dropwise. The reaction was allowed to come to room temperature and stirred and then stirred for one hour. 4-Fluoronitrobenzene (23.6 mL) was added and the solution was refluxed for 16 hours. The reaction was cooled to room temperature and 5 mL of isopropanol were added. The reaction was diluted with 6 liters of hexane and was washed twice with brine. The organic layer was dried over anhydrous magnesium sulfate, filtered and the solvents removed in vacuo to yield 226.4 grams of the desired product as a yellow oil.

EXAMPLE 3

Preparation of

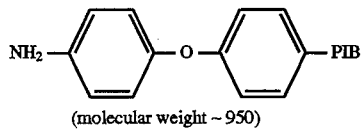

(molecular weight ~ 950)

A solution of 221.8 grams of the product from Example 2 in one liter of ethyl acetate containing 10.0 grams of 10% palladium on charcoal was hydrogenolyzed at 35–40 psi for 16 hours on a Parr low-pressure hydrogenator. Catalyst filtration and removal of the solvent in vacuo yield 208.1 grams of the desired product as a yellow oil. $^1$H NMR (CDCl$_3$) d 7.25 (d, 2H), 6.85 (AB quartet, 4H), 6.65 (d, 2H), 3.6 (bs, 2H), 0.7–1.8 (m, 137H).

EXAMPLE 4

Preparation of

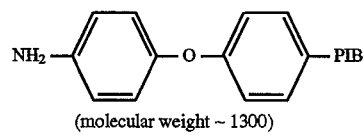

(molecular weight ~ 1300)

The procedures of Examples 1–3 were repeated using Ultravis 30 polyisobutene (molecular weight 1300, available from British Petroleum) in Example 1 instead of Ultravis 10 polyisobutene. $^1$H NMR (CDCl$_3$) d 7.25 (d, 2H), 6.85 (AB quartet, 4H), 6.65 (d, 2H), 3.5 (bs, 2H), 0.7–1.8 (m, 185H).

EXAMPLE 5

Preparation of

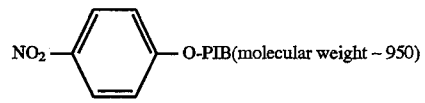

To a flask equipped with a magnetic stirrer, reflux condensor, nitrogen inlet and addition funnel was added 3.8 grams of a 35 weight percent dispersion of potassium hydride in mineral oil. The mineral oil was removed from the potassium hydride with anhydrous hexane. 300 milliliters of anhydrous tetrahydrofuran was added and the resulting suspension was cooled to 0° C. Polyisobutanol (21.0 grams, molecular weight average 984, prepared via hydroformylation of Amoco H-100 polyisobutene) dissolved in 200 mL of anhydrous tetrahydrofuran was added dropwise. The reaction was allowed to come to room temperature and stirred and then stirred for two hours. 4-Fluoronitrobenzene (3.7 mL) was added and the solution was refluxed for 16 hours. The reaction was cooled to room temperature and 1 mL of isopropanol was added. The reaction was diluted with 1.5 liters of hexane and was washed twice with brine. The organic layer was dried over anhydrous magnesium sulfate, filtered and the solvents removed in vacuo. The oil was chromatographed on silica gel, eluting with hexane/ethyl acetate (90:10) to yield 20.9 grams of the desired product as a brown oil.

EXAMPLE 6

Preparation of

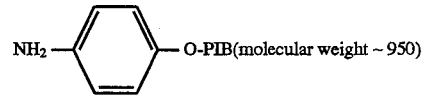

A solution of 16.2 grams of the product from Example 5 in 200 mL of ethyl acetate containing 2.0 grams of 10% palladium on charcoal was hydrogenolyzed at 35–40 psi for 16 hours on a Parr low-pressure hydrogenator. Catalyst filtration and removal of the solvent in vacuo yield 15.8 grams of the desired product as a yellow oil. $^1$H NMR (CDCl$_3$/D$_2$O) d 6.7 (AB quartet, 4H), 6.65 (d, 2H), 3.85 (t, 2H), 0.7–1.8 (m, 137H).

EXAMPLE 7

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was substracted from the weight of the valve at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

Single-Cylinder Engine Test Results

| Sample[1] | Intake Valve Deposit Weight (in milligrams) | | |
|---|---|---|---|
| | Run 1 | Run 2 | Average |
| Base Fuel | 282.2 | 272.0 | 277.1 |
| Example 2 | 24.7 | 12.1 | 18.4 |
| Example 4 | 26.2 | 18.4 | 22.3 |
| Example 6 | 13.2 | 40.0 | 26.6 |

[1]At 150 parts per million actives (ppma).

The base fuel employed in the above single-cylinder engine tests was a regular octane unleaded gasoline containing no fuel detergent. The test compounds were admixed with the base fuel to give a concentration of 150 ppma (parts per million actives).

The data in Table I illustrates the significant reduction in intake valve deposits provided by the substituted aromatic polyalkyl ethers of the present invention (Examples 2, 4, and 6) compared to the base fuel.

What is claimed is:

1. A fuel-soluble compound of the formula:

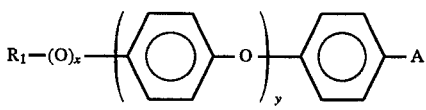

wherein $R_1$ is a polyalkyl group having an average molecular weight of about 450 to about 5,000;

A is nitro, amino, cyano, aminomethyl, N-alkylamino or N-alkylaminomethyl wherein the alkyl group contains from about 1 to about 6 carbon atoms, or N,N-dialkylamino or N,N-dialkylaminomethyl wherein each alkyl group independently contains from about 1 to about 6 carbon atoms.

x is an integer from about 0 to about 1; and y is an integer from about 0 to about 10 with the proviso that one of x and y must be 0 and the other must be greater than 0.

2. The compound according to claim 1, wherein $R_1$ is a polyalkyl group having an average molecular weight of about 700 to about 5,000.

3. The compound according to claim 2, wherein $R_1$ is a polyalkyl group having an average molecular weight of about 700 to about 3,000.

4. The compound according to claim 3, wherein $R_1$ is a polyalkyl group having an average molecular weight of about 900 to about 2,500.

5. The compound according to claim 1, wherein $R_1$ is a polyisobutyl group.

6. The compound according to claim 1, wherein x is about 0 and y is an integer of from about 1 to about 10.

7. The compound according to claim 1, wherein x is about 1 and y is about 0.

8. The compound according to claim 1, wherein A is nitro, amino, cyano or aminomethyl.

9. The compound according to claim 8, wherein A is nitro or amino.

10. A fuel composition comprising a major amount of hydrocarbons boiling in the gasoline or diesel fuel range and an effective deposit-controlling amount of a fuel-soluble compound of the formula:

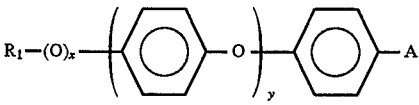

wherein $R_1$ is a polyalkyl group having an average molecular weight of about 450 to about 5,000;

A is nitro, amino, cyano, aminomethyl, N-alkylamino or N-alkylaminomethyl wherein the alkyl group contains from about 1 to about 6 carbon atoms, or N,N-dialkylamino or N,N-dialkylaminomethyl wherein each alkyl group independently contains from about 1 to about 6 carbon atoms x is an integer from about 0 to about 1; and y is an integer from about 0 to about 10 with the proviso that one of x and y must be 0 and the other must be greater than 0.

11. The fuel composition according to claim 10, wherein $R_1$ is a polyalkyl group having an average molecular weight of about 700 to about 5,000.

12. The fuel composition according to claim 11, wherein $R_1$ is a polyalkyl group having an average molecular weight of about 700 to about 3,000.

13. The fuel composition according to claim 12, wherein $R_1$ is a polyalkyl group having an average molecular weight of about 900 to about 2,500.

14. The fuel composition according to claim 10, wherein $R_1$ is a polyisobutyl group.

15. The fuel composition according to claim 10, wherein x is 0 and y is an integer of from about 1 to about 10.

16. The fuel composition according to claim 10, wherein x is about 1 and y is about 0.

17. The fuel composition according to claim 10, wherein A is nitro, amino, cyano, or aminomethyl.

18. The fuel composition according to claim 17, wherein A is nitro or amino.

19. The fuel composition according to claim 10, wherein the composition contains from about 50 to about 2,500 parts per million by weight of the fuel-soluble compound.

20. The fuel composition according to claim 10, wherein the composition further contains from about 100 to about 5,000 parts per million by weight of a fuel-soluble, non-volatile carrier fluid.

21. A fuel concentrate comprising an inert stable oleophilic organic solvent boiling in the range of from about 150° F. to about 400° F. and from about 10 to about 70 weight percent of a fuel-soluble compound of the formula:

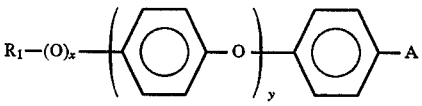

wherein $R_1$ is a polyalkyl group having an average molecular weight of about 450 to about 5,000;

A is nitro, amino, cyano, aminomethyl, N-alkylamino or N-alkylaminomethyl wherein the alkyl group contains from about 1 to about 6 carbon atoms, or N,N-dialkylamino or N,N-dialkylaminomethyi wherein each alkyl group independently contains from about 1 to about 6 carbon atoms, x is an integer from about 0 to about 1; and y is an integer from about 0 to about 10 with the proviso that one of x and y must be 0 and the other must be greater than 0.

22. The fuel concentrate according to claim 21, wherein $R_1$ is a polyalkyl group having an average molecular weight of about 700 to about 5,000.

23. The fuel concentrate according to claim 22, wherein $R_1$ is a polyalkyl group having an average molecular weight of about 700 to about 3,000.

24. The fuel concentrate according to claim 23, wherein $R_1$ is a polyalkyl group having an average molecular weight of about 900 to about 2,500.

25. The fuel concentrate according to claim 21, wherein $R_1$ is a polyisobutyl group.

26. The fuel concentrate according to claim 21, wherein x is 0 and y is an integer of from about 1 to about 10.

27. The fuel concentrate according to claim 21, wherein x is 1 and y is about 0.

28. The fuel concentrate according to claim 21, wherein A is nitro, amino, cyano, or aminomethyl.

29. The fuel concentrate according to claim 28, wherein A is nitro or amino.

30. The fuel concentrate according to claim 21, wherein the fuel concentrate further contains from about 20 to about 60 weight percent of a fuel-soluble, nonvolatile carrier fluid.

* * * * *